United States Patent [19]

Simon et al.

[11] Patent Number: 5,847,131
[45] Date of Patent: Dec. 8, 1998

[54] PREPARATION OF N-SUBSTITUTED CYCLIC AMINES

[75] Inventors: Joachim Simon, Mannheim; Roman Dostalek, Römerberg; Heinz Lingk, Bobenheim-Roxheim; Rainer Becker, Bad Dürkheim; Andreas Henne, Neustadt; Rolf Lebkücher, Mannheim; Cristina Freire Erdbrügger, Freinsheim; Michael Hesse, Worms; Detlef Kratz, Heidelberg, all of Germany

[73] Assignee: BASF Aktiengesellschaft, Ludwigshafen, Germany

[21] Appl. No.: 876,329

[22] Filed: Jun. 16, 1997

[30] Foreign Application Priority Data

Jun. 18, 1996 [DE] Germany .................. 196 24 283.5

[51] Int. Cl.⁶ .................. C07D 295/02; C07D 295/023
[52] U.S. Cl. .................................. 544/178; 546/184
[58] Field of Search ............... 546/184; 544/178

[56] References Cited

U.S. PATENT DOCUMENTS

| | | | |
|---|---|---|---|
| 4,739,051 | 4/1988 | Schroeder et al. | 544/106 |
| 4,910,304 | 3/1990 | Fischer et al. | 544/178 |
| 5,110,928 | 5/1992 | Schroeder et al. | 544/395 |

FOREIGN PATENT DOCUMENTS

| | | |
|---|---|---|
| 127 478 | 4/1985 | European Pat. Off. . |
| 440 829 | 8/1991 | European Pat. Off. . |
| 1106084 | 3/1968 | United Kingdom . |
| 95/32171 | 11/1995 | WIPO . |

*Primary Examiner*—Fiona T. Powers
*Attorney, Agent, or Firm*—Keil & Weinkauf

[57] ABSTRACT

N-Substituted cyclic amines are prepared by reacting diols with primary amines over a copper-containing catalyst which is obtainable by impregnation of an inert support with an aqueous solution of an ammine complex of a readily thermally decomposable copper compound and subsequent drying and calcination and contains from 5 to 50% by weight of copper, calculated as CuO.

8 Claims, No Drawings

PREPARATION OF N-SUBSTITUTED CYCLIC AMINES

Preparation of N-substituted cyclic amines

The present invention relates to a process for preparing N-substituted cyclic amines by reacting diols with primary amines over a copper-containing catalyst which is obtainable by impregnation of a support with an aqueous solution of an ammine complex of a readily thermally decomposable copper compound and subsequent drying and calcination and contains from 5 to 50% by weight of copper, calculated as CuO.

Processes for preparing N-substituted cyclic amines are known. Thus, N-methylated cyclic amines can be prepared by reacting the free amine with formaldehyde or methanol (U.S. Pat. No. 3,167,551). This process is thus multistage and is therefore technically complicated.

In comparison, those processes in which diols are reacted with methylamine in the presence of a catalyst to give N-methyl-substituted cyclic amines are better. Catalysts which are suitable for this purpose include both dehydrating catalysts such as phosphorus compounds and also hydrogenating-dehydrogenating catalysts based on, for example, copper, nickel, cobalt or mixtures comprising these elements.

Thus, for instance, according to BE-A-842 461 a diol is reacted batchwise with methylamine in the liquid phase in the presence of a phosphorus compound to give the N-methylated cyclic amine. This requires high temperatures (up to 350° C.) and very high pressures (up to 280 bar) in order to achieve reasonably satisfactory yields.

Catalysts which are more suitable for the reaction are hydrogenating-dehydrogenating catalysts based on copper or nickel. Thus, for example, GB-B 1 106 084 describes the batchwise reaction of diethylene glycol with monomethylamine over a CuO/ZnO catalyst which, at 300° C. and a pressure of from 100 to 200 bar, gives N-methylmorpholine in a yield of barely 40%.

U.S. Pat. No. 3,709,881 discloses that the reaction of diethylene glycol with alkylamines over a nickel catalyst at 100 bar and from 225 to 250° C. leads to N-alkylmorpholine in a yield of from 20 to 60%.

Furthermore, it is known from EP-A 440 829 (=U.S. Pat. No. 4 910 304) that N-substituted cyclic amines can be prepared from diols and alkylamines over a catalyst whose active composition comprises at least 80% by weight of copper in the presence of a catalytic amount of a basic alkali metal or alkaline earth metal compound. Continuous reaction of 1,5-pentanediol with monomethylamine at 245° C. and a hydrogen partial pressure of 120 bar at a total pressure of 250 bar gives N-methylpiperidine in a yield of 95%. Diethylene glycol and monomethylamine give, under otherwise identical conditions, N-methylmorpholine in a yield of 98%.

Although these yields meet industrial requirements, the high-copper catalysts described in the above application have the considerable disadvantage that the initially very high activity is virtually completely lost over a period of a few days, with the catalyst disintegrating to a copper sludge (see Examples). The high costs which are associated with frequent change of catalyst make the process economically uninteresting.

If the process is carried out using copper-containing supported catalysts, these are obtained by impregnation with copper salt solutions. This makes relatively high calcination temperatures necessary, as a result of which the catalyst particles are adversely affected and their activity is thus reduced.

It is an object of the present invention to provide a process for preparing N-substituted cyclic amines which can be carried out technically simply and economically.

We have found that this object is achieved by use of a specific hydrogenation/dehydrogenation catalyst which is obtainable by impregnation of an inert support with an aqueous solution of an ammine complex of a readily thermally decomposable copper compound and subsequent drying and calcination and contains merely from 5 to 50% by weight of copper, calculated as CuO. The specific catalyst is known from WO-A-95/32171 as a hydrogenation catalyst for the preparation of alcohols from the corresponding carbonyl compounds.

The present invention accordingly provides a process for preparing N-substituted cyclic amines of the formula I

where

A is an alkylene group or a —$(CH_2)_n$—[O—$(CH_2)_m$]$_r$— group which may each be substituted by one or more identical or different radicals $R^1$, and $R^1$ and $R^2$ are, independently of one another, alkyl, alkoxyalkyl, unsubstituted or alkyl- or alkoxy-substituted cycloalkyl, cycloalkylalkyl, aryl or arylalkyl, n,m are each, independently of one another, a number in the range from 2 to 8 and r is a number in the range from 1 to 3, by reacting primary amines of the general formula II

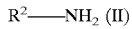
$R^2$——$NH_2$ (II)

with a diol of the general formula III

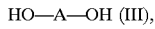
HO—A—OH (III), where $R^2$ and A are as defined above, in the presence of hydrogen and a copper-containing catalyst, wherein the catalyst used is obtainable by impregnation of an inert support with an aqueous solution of an ammine complex of a readily thermally decomposable copper compound and subsequent drying and calcination and contains from 5 to 50% by weight of copper, calculated as CuO, based on the total weight of the calcined catalyst.

The substituents in the formulae I to III have the following meanings:

A is:

an alkylene group such as a $C_4$—$C_{12}$-alkylene group, eg. —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, with $C_4$—$C_8$—alkylene groups being preferred, a —$(CH_2)_n$—[O—$(CH_2)_m$]$_r$—group in which n and m are each, independently of one another, from 2 to 8 and r is from 1 to 3, where the —$(CH_2)_n$—[O—$(CH_2)_m$]$_r$—group preferably has from 5 to 12 atoms in the chain and, preferably, n and m are each, independently of one another, from 2 to 4 and r is 1 or 2, for example —$(CH_2)_2$—O—$(CH_2)_2$—, —$(CH_2)_3$—O—$(CH_2)_2$—, —$(CH_2)_3$—O—$(CH_2)_3$—, —$(CH_2)_4$—O—$(CH_2)_2$—, —$(CH_2)_4$—O—$(CH_2)_3$—, —$(CH_2)_4$—O—$(CH_2)_4$— and —$(CH_2)_2$—O—$(CH_2)_2$—O—$(CH_2)_2$—. A can be substituted by one or more radicals $R^1$, where the radicals $R^1$ in a defined compound do not have to be the same. Preference is given to from 1 to 6 radicals $R^1$, particularly preferably from 1 to 4.

$R^1$ and $R^2$ are, independently of one another:

alkyl, such as unbranched or branched $C_1$–$C_{30}$-alkyl, preferably unbranched or branched $C_1$–$C_{20}$-alkyl, particularly preferably unbranched or branched $C_1$–$C_{12}$-alkyl such as methyl, ethyl, n-propyl, iso-propyl, n-butyl, iso-butyl, sec-butyl, tert-butyl, n-pentyl, iso-pentyl, sec-pentyl, tert-pentyl, neo-pentyl, 1,2-dimethylpropyl, n-hexyl, iso-hexyl, sec-hexyl, n-heptyl, iso-heptyl, n-octyl, iso-octyl, n-nonyl, iso-nonyl, n-decyl, iso-decyl, n-undecyl, iso-undecyl, n-dodecyl and iso-dodecyl.

alkoxyalkyl, preferably $C_2$–$C_{20}$-alkoxyalkyl such as methoxymethyl, ethoxypropyl and butoxydecyl, cycloalkyl, preferably $C_3$–$C_{20}$-cycloalkyl, particularly preferably $C_3$–$C_8$-cycloalkyl such as cyclopropyl, cyclobutyl, cyclopentyl, cyclohexyl, cycloheptyl and cyclooctyl, alkylcycloalkyl, preferably $C_4$–$C_{20}$-alkylcycloalkyl where the cycloalkyl group has from 3 to 8, preferably from 3 to 6, carbon atoms, for example methylcyclopropyl, isopropylcyclohexyl and dodecylcyclohexyl, cycloalkylalkyl, preferably $C_4$–$C_{20}$-cycloalkylalkyl where the alkyl group has from 1 to 14, preferably from 1 to 10, carbon atoms, for example cyclopropylmethyl, cyclopentylmethyl, cyclohexylmethyl, cyclopropylethyl, cyclopentylethyl and cyclohexylethyl, aryl such as phenyl, 1-naphthyl, 2-naphthyl, 1-anthryl, 2-anthryl and 9-anthryl, preferably phenyl, arylalkyl, preferably $C_7$–$C_{20}$-arylalkyl, particularly preferably $C_7$–$C_{20}$-phenylalkyl such as benzyl, phenethyl or phenyldecyl.

Final products of the formula I are, for example:
N-methylpyrrolidine, N-ethylpyrrolidine, N-methylpiperidine, N-ethylpiperidine, N-methylmorpholine, 1-methyl-1-azacycloundecane and N-n-butylmorpholine. The process is particularly preferred for preparing N-methyl-substituted cyclic amine compounds.

Starting materials of the formula II are, for example:
methylamine, ethylamine, n-propylamine, iso-propylamine, n-butylamine, isobutylamine, n-dodecylamine, aniline and p-toluidine.

Starting materials of the formula III are, for example:
1,4-butanediol, 3-methylpentane-1,5-diol, diethylene glycol (3-oxapentane-1,5-diol), dibutylene glycol (5-oxanonane-1,9-diol), triethylene glycol (3,5-dioxaheptane-1,7-diol), 1,3-dipropylene glycol (4-oxaheptane-1,7-diol), dipropylene glycol (1,5-dimethyl-3-oxapentane-1,5-diol), 5-oxanonane-1,9-diol and 2,5-hexanediol.

In general, the suitable diols III are those having primary or secondary hydroxyl groups, particularly those having primary hydroxyl groups, ie. a,ω-diols.

The reaction proceeds according to the general reaction equation [1] shown below:

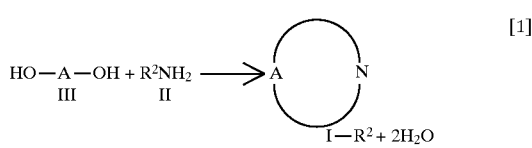

The reaction is carried out in the presence of hydrogen, batchwise or preferably continuously in the liquid phase at from 200° to 300° C., preferably from 220° to 280° C., and a pressure of from 100 to 300 bar, preferably from 200 to 250 bar, or in the gas phase at from 200° to 300° C., preferably from 200° to 250° C., and a pressure of from 1 to 50 bar, preferably from 10 to 30 bar. The liquid-phase reaction can be carried out as a suspension reaction or in the downflow or upflow mode. It is advisable to use monoalkylamines II or diols III which have a low volatility or are solid as solutions in an inert solvent, with from 50 to 200 ml, preferably from 100 to 150 ml, of an inert solvent per mol of II or III generally being sufficient.

Suitable inert solvents are ethers such as diethyl ether, methyl isopropyl ether, methyl tert-butyl ether, tetrahydrofuran and dioxane; aliphatic hydrocarbons such as n-pentane, a pentane isomer mixture, n-hexane, a hexane isomer mixture, petroleum ether and cyclohexane, aromatic hydrocarbons such as benzene, toluene, the xylenes and their isomer mixtures, or mixtures of these.

In the batchwise procedure, the catalyst is preferably used in the form of a finely divided suspension. The amount of catalyst used is from 3 to 30 g, preferably from 10 to 15 g, of copper per kg of diol. The diol III together with the catalyst suspended therein can be initially charged in water and the amine II can be gradually added thereto as required for the reaction at the reaction temperature under the conditions selected. When using the reactants in equimolar amounts, the components diol, amine and water can also be initially charged together.

In the continuous procedure, the catalyst is used as a fixed bed in the form of beads, extrudates, pellets or rings. The amount of catalyst is in the range from 100 to 1000, preferably from 200 to 400, g of copper per kg of diol per hour. Particular preference is given to fixed-bed catalysts which are operated in the downflow mode or in the upflow mode in which the entire catalyst bed should be covered by a continuous liquid phase. In this embodiment, the diol III and the amine II are then passed over the catalyst fixed bed in the selected molar ratio.

The molar ratio of monoalkylamine to the diol is generally in the range from 1:1 to 2:1, preferably from 1.1:1 to 1.5:1.

Hydrogenation/dehydrogenation catalysts which can be used are described in WO-A-95/32171, the entire contents of which are hereby incorporated by reference. Accordingly, they can be prepared in various ways. However, particular preference is given to impregnation of a support for from 2 to 60 minutes, preferably from 5 to 30 minutes, with an aqueous solution of a readily thermally decomposable copper compound which completely covers the support, and subsequent drying and calcination at from 200° to 400° C., preferably from 250° to 350° C., particularly preferably at 300° C.

The impregnation using a solution which completely covers the support leads to relatively uniform impregnation of the support material and thus to a finer and more uniform distribution of the copper in or on the support. The formation of nonuniform concentration profiles over the cross-section of the support material, as can occur in other impregnation methods, are avoided in this method, which makes the preparation of the catalyst to be used according to the present invention more reproducible and as a result more economical.

Support materials which can be used are those customarily employed, for example $SiO_2$, silicates, pumice, diatomaceous earth, silica gel, aluminum oxide, zeolites and zirconium dioxide, with particular preference being given to $SiO_2$-containing supports. The support material used for the catalyst is described as $SiO_2$-containing if it comprises $SiO_2$ or a silicate such as magnesium silicate. Since the anionic silicate groups are present in the catalyst in a combination of monomeric, oligomeric and polymeric forms, they are analytically determined and calculated as $SiO_2$.

For the purposes of the present invention, readily thermally decomposable copper compounds are copper compounds which decompose at calcination temperatures of from 200° to 400° C., preferably from 250° to 350° C., to give oxidic copper compounds or elemental copper. Examples which may be mentioned of such compounds are copper carbonate, copper oxalate or copper formate.

For the purposes of the present invention, copper carbonate is basic copper carbonate. It can be obtained, for example, by precipitation of copper(II) salts with sodium carbonate solution. These copper salts are used in the form of their relatively stable, readily water-soluble ammine complexes. These include complexes with ammonia or amines. Particular preference is given to using ammoniacal copper carbonate solution for this purpose. The use of these readily thermally decomposable copper compounds makes it possible to carry out the calcination at the low temperatures specified, while copper salts conventionally used for the impregnation, eg. copper nitrate or copper sulfate, generally require calcination temperatures of about 500° C. Both the use of readily thermally decomposable copper compounds and the use of low calcination temperatures makes it possible to produce small, uniformly distributed copper crystallites and thus a relatively high catalytically active copper surface area in the finished catalyst.

The advantageous effect of this enlarged catalytically active copper surface area is demonstrated, inter alia, by comparison of the Examples 1.1 (process of the present invention) and 1.4 (prior art, catalyst obtained by impregnation with copper nitrate solution and calcination at 500° C.) described below. The process of the present invention gives significantly higher yields than that corresponding to the prior art.

A measure of the effective copper surface area for a certain amount of copper used is the dispersion. It is defined as the ratio of the number of copper atoms at the surface of the copper crystallites to the total number of copper atoms in the copper crystallites of the support.

The dispersion of the copper in a catalyst can be determined directly from the size of the crystallites or indirectly from the amount of oxygen required for oxidation of the copper surface and the amount of copper used in the impregnation.

Apart from an increased dispersion, the catalysts prepared as described in WO-A-95/32171 also have improved mechanical stability. The increased mechanical stability is reflected, in particular, in an increased hardness and reduced abrasion of the catalyst.

The copper catalyst contains from 5 to 50, preferably from 15 to 40, particularly preferably from 20 to 30, % by weight of copper, calculated as CuO, based on the total weight of the calcined catalyst. It additionally contains from 50 to 95, preferably from 60 to 85, particularly preferably from 70 to 80, % by weight of silicon, calculated as $SiO_2$, based on the total weight of the calcined catalyst.

The catalyst is preferably reduced in situ with hydrogen and thus converted into the active form. Particular preference is given to a catalyst which, in this state, has a copper surface area of >20 $m^2/g$, a particle size of <100 nm and a Cu dispersion of >20%.

After the reaction, the products are isolated by customary methods, eg. by distillation or extraction from the reaction mixture; unreacted starting materials may be returned to the reaction.

The following Examples illustrate the invention without restricting it thereto.

EXAMPLES

Preparation of the catalyst:

The catalyst is obtained by impregnating 1 l (0.45 kg) of $SiO_2$ spheres having a diameter of from 3 to 5 mm at room temperature with 1 l of 35% strength, aqueous ammonia solution in which 151 g of basic copper carbonate (calculated as $2CuCO_3 \cdot Cu(OH)_2$) has been dissolved. The impregnation is carried out for 15 minutes in a solution which completely covers the support. The impregnated spheres are dried for 5 hours at 120° C. and then calcined for 2 hours at 300° C. These impregnation and calcination steps are repeated once and give 1 l (0.62 kg) of finished catalyst comprising 30% by weight of CuO on 70% by weight of $SiO_2$.

1. Preparation of N-methylmorpholine:

EXAMPLE 1.1

80 ml/h of monomethylamine and 210 ml/h of diethylene glycol are passed at 280° C., 200 bar total pressure and 100 bar hydrogen partial pressure in the downflow mode through a tube reactor having an internal diameter of 3.2 cm and a height of 125 cm and containing a bed of 700 ml of the above-described catalyst reduced with hydrogen in the form of 3–5 mm beads. After a running time of 14 ½ days, the yield of N-methylmorpholine is 82% of theory. The catalyst removed from the reactor shows no mechanical changes.

EXAMPLE 1.2

130 ml/h of monomethylamine, 200 ml of diethylene glycol and 300 ml/h of hydrogen are passed in the gas phase at 200° C. and 20 bar total pressure through a tube reactor having an internal diameter of 4.1 cm and a height of 350 cm and containing a bed of 1000 ml of the above-described catalyst reduced with hydrogen in the form of 3–5 mm beads. After a running time of 4 ½ days, the yield of N-methylmorpholine is 11% of theory. The catalyst removed from the reactor shows no mechanical changes.

EXAMPLE 1.3 (PRIOR ART)

80 ml/h of monomethylamine and 210 ml/h of diethylene glycol are passed at 280° C., 200 bar total pressure and 100 bar hydrogen partial pressure in the downflow mode through a tube reactor having an internal diameter of 3.2 cm and a height of 125 cm and containing a bed of 700 ml of the catalyst described in EP-A 440 829 on p. 5, lines 16–20, and reduced with hydrogen in the form of 3×5 mm pellets. After a running time of 14 ½ days, the yield of N-methylmorpholine is 69% of theory. The catalyst removed from the reactor has completely disintegrated to a red sludge.

EXAMPLE 1.4 (PRIOR ART, IMPREGNATED CATALYSTS, COMPARISON WITH EXAMPLE 1.1)

Preparation of the catalyst

The catalyst is obtained according to a known literature method (see, for example, Berkman, Morrell and Egloff, "Catalysis", 1940) by impregnation of γ-$Al_2O_3$ with a copper nitrate solution and subsequent calcination at 500° C. The finished catalyst contains 16% of CuO.

Preparation of N-methylmorpholine 80 ml/h of monomethylamine and 210 ml/h of diethylene glycol are passed at 280° C., 200 bar total pressure and 100 bar hydrogen partial pressure in the downflow mode through a tube reactor having an internal diameter of 3.2 cm and a height of 125 cm and containing a bed of 700 ml of the above-described catalyst in the form of 4 mm extrudates. After a running time of 10 days, the yield of N-methylmorpholine is barely 35% of theory. The catalyst removed from the reactor shows no mechanical changes.

2. Preparation of N-methylpiperidine:

EXAMPLE 2.1

130 ml/h of monomethylamine and 210 ml/h of 1,5-pentanediol are passed at 240° C., 200 bar total pressure and 70 bar hydrogen partial pressure in the upflow mode through a tube reactor having an internal diameter of 3.2 cm and a height of 125 cm and containing a bed of 700 ml of the catalyst used in Example 1.1 and reduced with hydrogen in the form of 3–5 mm beads. After a running time of 40 days, the yield of N-methylpiperidine is 82% of theory. The catalyst removed from the reactor shows no mechanical changes.

EXAMPLE 2.2 (PRIOR ART)

120 ml/h of monomethylamine and 210 ml/h of 1,5-pentanediol were passed at 240° C., 200 bar total pressure and 80 bar hydrogen partial pressure in the upflow mode through a tube reactor having an internal diameter of 3.2 cm and a height of 125 cm and containing a bed of 700 ml of the catalyst described in EP-A 440 829 on p. 5, lines 16–20 and reduced with hydrogen in the form of 3×5 mm pellets. After a running time of 10 days, the yield of N-methylpiperidine is 62% of theory. The catalyst removed from the reactor has completely disintegrated to a red sludge.

We claim:

1. A process for preparing N-substituted cyclic amines of the formula I

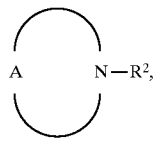

where

A is an alkylene group or a —$(CH_2)_n$—[O—$(CH_2)_m$]$_r$— group which may each be substituted by one or more identical or different radicals $R^1$, and $R^1$ and $R^2$ are, independently of one another, alkyl, alkoxyalkyl, unsubstituted or alkyl- or alkoxy-substituted cycloalkyl, cycloalkylalkyl, aryl or arylalkyl, n,m are each, independently of one another, a number in the range from 2 to 8 and r is a number in the range from 1 to 3, by reacting primary amines of the general formula II

with a diol of the general formula III

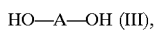

where $R^2$ and A are as defined above, in the presence of hydrogen and a copper-containing catalyst, wherein the catalyst used is obtainable by impregnation of an inert support with an aqueous solution of an ammine complex of a readily thermally decomposable copper compound and subsequent drying and calcination and contains from 5 to 50% by weight of copper, calculated as CuO, based on the total weight of the calcined catalyst.

2. A process as claimed in claim 1, wherein the readily thermally decomposable copper compound used is copper carbonate, copper oxalate and/or copper formate.

3. A process as claimed in claim 1, wherein the catalyst used contains from 20 to 30% by weight of copper, calculated as CuO, based on the total weight of the calcined catalyst.

4. A process as claimed in claim 1, wherein the reactions carried out in the liquid phase at from 200° to 300° C., and a pressure of from 100 to 300 bar.

5. A process as claimed in claim 1, wherein the reaction is carried out in the gas phase at from 200° to 300° C., and a pressure of from 1 to 50 bar.

6. A process as claimed in claim 1, wherein the reaction is carried out continuously.

7. The process of claim 4 wherein the temperature is from 200° to 280° and the pressure is from 200 to 250 bar.

8. The process of claim 5 wherein the temperature is from 200° to 250° C. and the pressure is from 10 to 30 bar.

* * * * *